Figure 1:
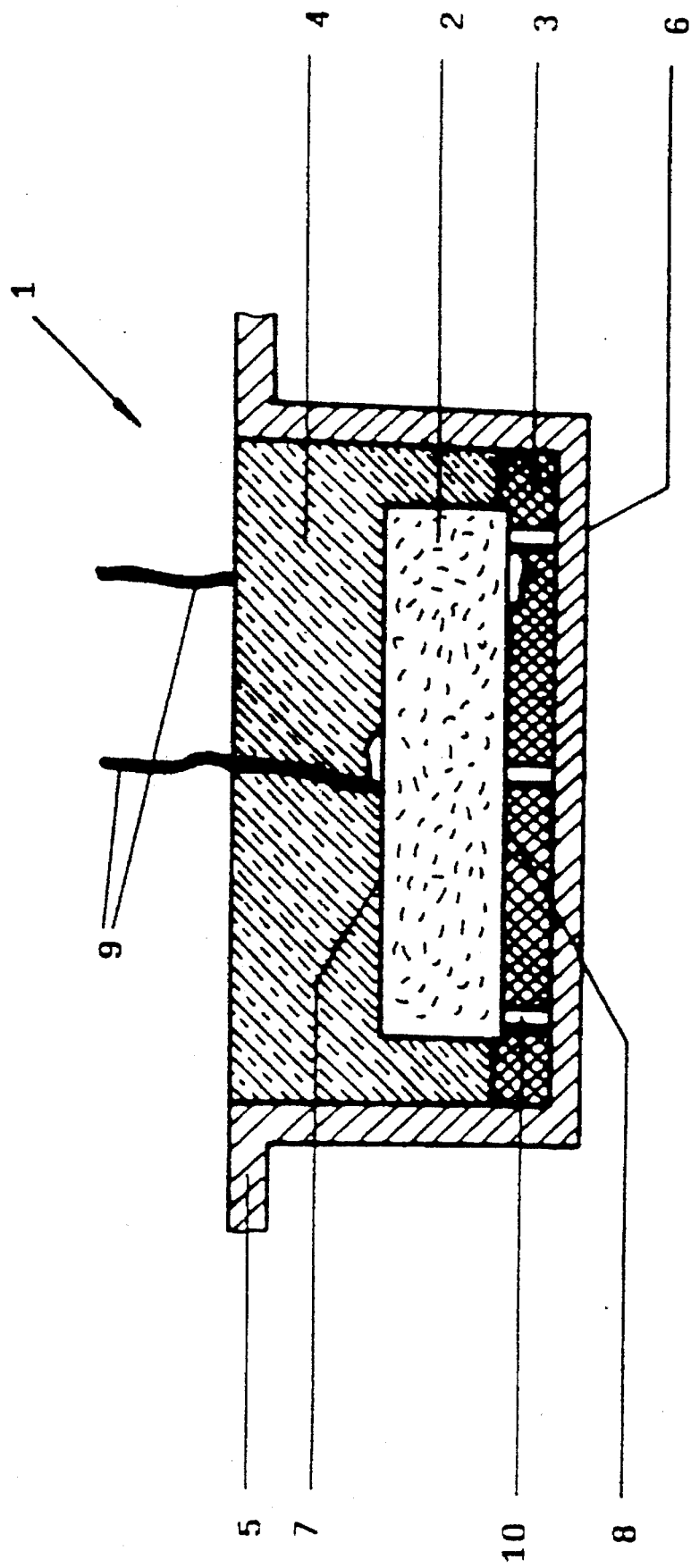

United States Patent

Müller et al.

Patent Number: 5,457,352
Date of Patent: Oct. 10, 1995

[54] ULTRASONIC CONVERTER

[75] Inventors: Roland Müller; Peter Klöfer, both of Steinen, Germany

[73] Assignee: Endress + Hauser GmbH + Co., Germany

[21] Appl. No.: 240,650
[22] PCT Filed: Sep. 11, 1993
[86] PCT No.: PCT/DE93/00853
§ 371 Date: May 13, 1994
§ 102(e) Date: May 13, 1994
[87] PCT Pub. No.: WO94/07236
PCT Pub. Date: Mar. 31, 1994

[30] Foreign Application Priority Data

Sep. 15, 1992 [DE] Germany ............ 42 30 773.2

[51] Int. Cl.$^6$ .................................... H01L 41/08
[52] U.S. Cl. ............................ 310/327; 310/334
[58] Field of Search ....................... 310/324, 326, 310/327, 334–337

[56] References Cited

U.S. PATENT DOCUMENTS

| 3,239,696 | 3/1966 | Burkhalter et al. | 310/327 X |
| 3,376,438 | 4/1968 | Colbert | 310/327 |
| 3,771,117 | 11/1973 | Shaffer et al. | 310/327 X |
| 4,536,673 | 8/1985 | Forster | 310/327 |
| 4,571,520 | 2/1986 | Saito et al. | 310/327 |
| 4,616,152 | 10/1986 | Saito et al. | 310/334 |
| 4,728,844 | 3/1988 | Wilson et al. | 310/327 |
| 5,274,296 | 12/1993 | Hiki et al. | 310/327 |

FOREIGN PATENT DOCUMENTS

| 9217071.4 | 3/1993 | Germany. |
| 60-012899 | 5/1985 | Japan. |
| 2097630 | 11/1982 | United Kingdom. |

Primary Examiner—Mark O. Budd
Attorney, Agent, or Firm—Barnes & Thornburg

[57] ABSTRACT

An ultrasonic converter (1) is proposed with a housing (5) and a cylindrical ceramic oscillator (2) of slight thickness with metal electrodes (7, 8), arranged at the front faces of the ceramic oscillator (2) and an adaptation layer (3) made of a synthetic material arranged between the front face of the ceramic oscillator (2) facing the irradiating medium and the membrane (6) of the ultrasonic converter (1) formed by the floor of the housing. The remaining free space of the housing (5) is filled with a synthetic damping layer (4) for damping the ceramic oscillator [2]. The innovation of the invention lies in that the damping layer (4) is formed from a silicon elastomer of high density with a large proportion of metal oxide, which can be mixed and applied mechanically during the gel phase of the adaptation layer (4).

6 Claims, 1 Drawing Sheet

ULTRASONIC CONVERTER

DESCRIPTION

The invention relates to an ultrasonic converter having a housing and a cylindrical ceramic oscillator of slight thickness at whose front faces metal electrodes are arranged and at one front face of which, facing the medium to be irradiated, an adaptation layer of a synthetic material is arranged which is in a form-fitting and operating connection with the membrane formed by the floor of the housing and whose remaining housing interior is filled with a damping layer of a synthetic material.

Due to the physical behavior of the ultrasonic converters acting as transmitting and receiving converters, these have the disadvantage that the measurement of the path between the membrane and the reflection plane is possible only up to a minimum distance. This means that a portion of the storage capacity of a container or of a storage area or the flow volume of the sluice can partially not be utilized because a monitoring of the fill and flow height within the minimum distance between the membrane and the reflection plane is not possible.

This minimum distance is determined in that in the case of converters operating with sonic pulses, the oscillations of the membrane at the end of the transmission pulse do not suddenly stop, but the membrane continues to oscillate for a little while longer. During the continuing oscillation time, however, no arriving echo pulses can be received or at least cannot be recognized. The timespan in which a reception or the evaluation of the echo pulse is not possible, is generally described as a blocking distance.

In the German Patent No. 3,301,848, for the reduction of the blocking distance, it is proposed to provide the entire ultrasonic converter with a foam casing made of a polyurethane foam except for the side of the synthetic adaptation layer facing the sound-emitting medium. Such a foam filler is to solve the task of influencing the oscillating behavior of the converter by damping the mechanical oscillation and thus to shorten the blocking distance. This takes place in that through the penetration of the sound wave into the polyurethane foam, a portion of the oscillation energy is lost and thus the oscillation behavior of the ceramic oscillator is reduced. However, the solution proposed in DE-PS 3,301,848 has the disadvantage that due to the varying density of ceramic material and polyurethane foam, only a very poor transition of the acoustic impedance of the ceramic oscillator to the foam casing is given. In particular, a disadvantage lies in that polyurethane foam is not temperature-resistant and for this reason, a usable reduction of the blocking distance can take place only during ideal constant temperatures, which rarely occur in practice.

According to further developments in the state of the art, as also described in DE-PS 3,301,848, the synthetic layer, which is for the adaptation of the acoustic impedance of the ceramic material to the acoustic impedance of the medium provided between the ceramic oscillator and the membrane in which the sound pulse is to be irradiated, consists of a polystyrene lacquer with embedded hollow spheres made of silicon dioxide. However, also epoxy resins and, as shown in column 1, line 36 of DE-PS 3,301,848, silicone elastomers have become known for this task. For example, Selastic E by the Dow Corning Co. represents a readily used material.

An additional disadvantage of the proposed damping of the ceramic oscillator with a polyurethane foam is that the material of the adaptation layer cannot bond with the material of the damping material and that, especially at high temperatures, quite frequently a detachment of the layers occurs.

For this reason, in the instructions proposed in DE-PS 3,301,848, the interior housings of this type of ultrasonic converter are frequently filled with a silicone elastomer, except for the side of the adaptation layer facing the irradiating medium. Such silicone elastomers, such as Eccosil 5952 of Grace Electronic Materials Co., have the advantage that the damping layer has a base which is chemically similar to the adaptation layer and thus, due to a significantly smaller difference between the acoustic impedance of the ceramic oscillator and the acoustic impedance of the damping layer, an easier penetration and absorption of the sound waves is made possible, which leads to a reduced oscillating behavior of the ceramic oscillator. An additional advantage for the use of these materials as a damping layer can be seen in their increased temperature resistance.

However, these materials also do not meet all requirements placed on them. For example, due to the extremely high mixing ratio (500:1) of base material to hardening agent, they cannot be processed by a machine. This means, they must be manually mixed and applied. The condensation cross-linking requires that the application of thick layers should be undertaken in several steps in order to permit an escape of the cleavage products (alcohols). Furthermore, the cleavage products may be diffused into the adaptation layer and there may lead to the formation of adhesion damage. The cross-linking may also be reversible at high temperatures, i.e., with high temperatures and the simultaneous occurrence of humidity, after an extended resting period, undesirable decomposition products may be released.

Thus, the task is solved only partially by the proposed solutions and the general state of the art.

In contrast thereto, the invention takes on the task of influencing the oscillation behavior of an ultrasonic converter by applying a damping layer in such a way, that an even shorter blocking distance is obtained and simultaneously the damping layer can be mixed and applied by machine. For this purpose, the damping layer is to form a nondetachable bond with the adaptation layer.

This task is solved by means of the characteristic cited in claim 1. Additional characteristics of the invention are cited in the subclaims.

Further advantages of the invention include that during the cross-linking, no cleavage products are released, and also thicker layers can be poured in a single work process, even at high temperatures and the simultaneous presence of humidity, no reaction products and reversible reactions can be triggered. A brief dripping time permits the rapid further processing of the damping layer following application.

The invention will be described in greater detail by means of the single drawing.

In the Figure, (1) represents the ultrasonic converter which is formed, as known, from the ceramic oscillator (2), the adaptation layer (3), the damping layer (4), and the housing (5) surrounding the ceramic oscillator (2) the adaptation layer (3) and the damping layer (4). The floor of the housing (5) simultaneously represents the membrane (6) of the ultrasonic converter (1). At the ceramic oscillator (2), on the two front faces, metal electrodes (7, 8) are attached. The connection lines (9), connected by means of a soldering connection to the metal electrodes (7, 8), are in electrical connection with an electronic circuit, not shown, by means of which the ceramic oscillator (2) is stimulated to oscillate with the frequency of the ultrasonic wave. At that time, across the same lines (9), also that alternating voltage which is given off by the ceramic oscillator (2) upon receiving the echo wave, is transferred to the electronic circuit, not shown.

Via the adaptation layer (3), the ceramic oscillator (2) stimulates the membrane (6) to oscillate in a pulse-like manner. However, following the end of the transmission pulse, these oscillations do not end abruptly but the ceramic oscillator (2) continues to oscillate for a little while longer. It can now be seen that the echo pulses that arrive at the membrane (6) during this continuing oscillation and that stimulate the ceramic oscillator (2) to oscillate via the adaptation layer (3) cannot be recognized as echo pulses. For this reason, it is desirable to dampen the oscillation behavior of the ceramic oscillator (2) in such a way that at the end of the transmission pulse, as rapid an oscillation as possible takes place, and thus the blocking distance is kept small. This is necessary so that also small distances between the membrane (6) and the reflection plane can be detected.

The damping of the ceramic oscillator (2) will take place with the aid of a damping layer (4) which surrounds the ceramic oscillator (2) except for the front surface (8) facing the irradiation media. At that time, the damping properties of the material of this damping layer (4) are assigned considerable significance. Surprisingly, it has been found that an addition of a cross-linked 2-component silicone elastomer with an extremely high solid material content, i.e, a high specific density, such as >2.00 g/cm$^3$, has the best damping properties for a ceramic oscillator (2).

In the example of the invention, the damping layer (4) is formed from a silicone elastomer which has a 70% proportion of a solid material of metal oxides. Such a silicone elastomer with a proportion of 65% $Al_2O_3$ and 5% $Fe_2O_3$ is particularly suited for this purpose.

The application of such a damping layer (4) with an extremely high solid content takes place in such a way that at first the interior of the housing (5) is sandblasted and cleaned. The sandblasting creates a rough surface on the floor and interior wall of the housing (5). Such a rough surface supports the adhesion of sealing compound layers applied to the housing. Following the subsequent cleaning and application of a base layer, its activation takes place at an increased temperature. When the housing (5) so prepared has been cooled to room temperature, the ceramic oscillator (2) can be used. At that time, steps are provided for keeping the ceramic oscillator (2) at a certain distance from the inside of the membrane (6), so that the adaptation layer (3), penetrating the space between the ceramic oscillator (2) and the membrane (6) in the hardened state assumes a thickness which corresponds to λ/4 of the ultrasonic wave. This is achieved in that in the housing (5) or also at the ceramic oscillator (2), short spacing pieces (10) made of a synthetic material are applied, on which the ceramic oscillator (2) is supported. The 2-component silicone elastomer of the adaptation layer (3), mechanically stirred and ventilated by means of a casting machine, is now brought together mechanically during the actual casting process and introduced into the housing (5). The introduction of the layers by means of a casting machine has the advantage that important factors of the casting process, such as the mixing ratio, the mass to be introduced, etc., can be adjusted and constantly monitored. This constitutes an advantage involving considerable labor savings when compared to the manual casting process. Upon introduction of the adaptation layer (3), the front surface (8) of the ceramic oscillator (2) facing the membrane (6), is completely covered by the adaptation layer (3) and the ceramic oscillator (2) is dipped somewhat into the adaptation layer (3).

During the casting of the adaptation layer (3), the application of the damping layer (4) can be already prepared. Since the latter also advantageously consists of a mechanically processed 2-component silicone elastomer, the acoustic parameters of the casting can also be set precisely. So, for example, the absorption coefficient [can be set] through the controlled introduction of precisely defined air bubbles, and across the density, the sound impedance [can] also [be set]. In the same way, the viscosity and the pot life can be adjusted in such a way that no air bubbles can arise during the cross-linking process. Since the adaptation layer (3) has a base which is chemically similar to the damping layer (4) the damping layer (4) can be already applied during the gel phase of the adaptation layer (3), resulting in a particularly good bond between both layers. The fact that no cleavage products are released during the cross-linking time makes it possible for the damping layer (4) to be applied in a single work process. The ultrasonic converter, which is complete after application of the damping layer, can be processed further after a very short period of time due to a very short pot life of the material of the damping layer (4).

An additional advantage of the proposed solution is that the damping layer (4) has an acoustic impedance due to the high oxidic proportions, which comes substantially closer to the acoustic impedance of the ceramic material. Due to this similarity, the sound wave emanating from the front face (7) of the ceramic oscillator (2) facing the damping layer (4) can easily penetrate the damping layer (4) in order to be completely absorbed there. This triggers such a brief drop in the oscillation amplitude in the oscillation behavior of the ceramic oscillator (2) that the oscillation behavior is thus substantially influenced and a shorter blocking distance is achieved.

The material proposed for the damping layer (4) also offers the advantage that the damping layer (4) has such a high absorption that the resonance frequencies of the ceramic oscillator (2) are completely suppressed at the front face (7) and at the portion of the cover surface of the ceramic oscillator (2) that is encased by the damping layer (4), which leads to the point that the resonance frequency can be effective only in the direction of the adaptation layer (3).

We claim:

1. Ultrasonic converter with a housing, a cylindrical ceramic oscillator of slight thickness, metal electrodes arranged at the front faces of the ceramic oscillator, an adaptation layer made of a synthetic material arranged at the front face of the ceramic oscillator, which faces the irradiating medium, which is form-fitting and operationally connected with the membrane of the ultrasonic oscillator formed by the floor of the housing, whose remaining interior space is filled by a damping layer made of a synthetic material, characterized in that the damping layer is formed from a silicone elastomer with a high proportion of metal oxides, the silicone elastomer having a proportion of at least 55% $Al_2O_3$ and of at least 2% $Fe_2O_3$.

2. Ultrasonic converter, in accordance with claim 1, characterized in that the damping layer (4) has a specific density of >2.00 g/cm$^3$.

3. Ultrasonic converter, in accordance with claim 1, characterized in that the damping layer (4) can be applied during the gel phase of the adaptation layer (3).

4. Ultrasonic converter, in accordance with claim 2, characterized in that the adaptation layer (3) and also the damping layer (4) have a chemical affinity in structure and composition.

5. Ultrasonic converter, in accordance with claim 2, characterized in that for determining the absorption coefficients of the damping layer (4), air bubbles may definitely be introduced.

6. Ultrasonic converter, in accordance with claim 1, characterized in that the damping layer (4) can be mixed and applied by machine.

* * * * *